United States Patent
Silvestro

(10) Patent No.: US 11,369,408 B2
(45) Date of Patent: Jun. 28, 2022

(54) ADJUSTABLE BLOCKAGE-CUTTING DEVICE

(71) Applicant: Medtronic Vascular, Inc., Santa Rosa, CA (US)

(72) Inventor: Claudio Silvestro, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 150 days.

(21) Appl. No.: 16/802,740

(22) Filed: Feb. 27, 2020

(65) Prior Publication Data

US 2021/0267626 A1 Sep. 2, 2021

(51) Int. Cl.
| | | |
|---|---|---|
| *A61B 17/3207* | (2006.01) | |
| *A61B 17/00* | (2006.01) | |
| *A61M 25/09* | (2006.01) | |

(52) U.S. Cl.
CPC ............ *A61B 17/320725* (2013.01); *A61B 2017/00557* (2013.01); *A61M 25/09* (2013.01)

(58) Field of Classification Search
CPC .......... A61B 17/3207; A61B 17/32075; A61B 17/320725
See application file for complete search history.

(56) References Cited

U.S. PATENT DOCUMENTS

| | | | | |
|---|---|---|---|---|
| 5,908,435 | A * | 6/1999 | Samuels | A61M 25/00 606/200 |
| 7,279,002 | B2 | 10/2007 | Shaw et al. | |
| 2003/0212384 | A1 * | 11/2003 | Hayden | A61M 29/02 604/533 |
| 2005/0080478 | A1 | 4/2005 | Barongan | |
| 2006/0178685 | A1 | 8/2006 | Melsheimer | |
| 2007/0198047 | A1 | 8/2007 | Schon et al. | |
| 2011/0034937 | A1 * | 2/2011 | Mustapha | A61F 2/958 606/127 |
| 2012/0130395 | A1 * | 5/2012 | Vardi | A61B 17/22 606/127 |
| 2013/0006284 | A1 | 1/2013 | Aggerholm et al. | |
| 2016/0262789 | A1 * | 9/2016 | Root | A61B 17/320725 |

FOREIGN PATENT DOCUMENTS

CN 110063768 A 7/2019

OTHER PUBLICATIONS

Extended European Search Report for European Application No. 21 15 8703, dated Jun. 22, 2021.

* cited by examiner

*Primary Examiner* — Tuan V Nguyen
(74) *Attorney, Agent, or Firm* — Brooks Kushman P.C.

(57) ABSTRACT

A catheter used for percutaneous endovascular procedures is described. The catheter is configured to be used for engagement and treatment of obstructive lesions in a patient's vasculature. The catheter includes a tube having a leading edge that is configured to score or cut a lesion in a vasculature. The tube may be an expandable outer tube, and placed around an inflatable inner tube, such that inflation of the inner tube expands the outer tube. Expansion of the inner tube may connect or laterally lock the inner tube to the outer tube, allowing both tubes to move in unison through the vasculature. The leading edge can score or cut lesions as it moves in the vasculature.

20 Claims, 3 Drawing Sheets

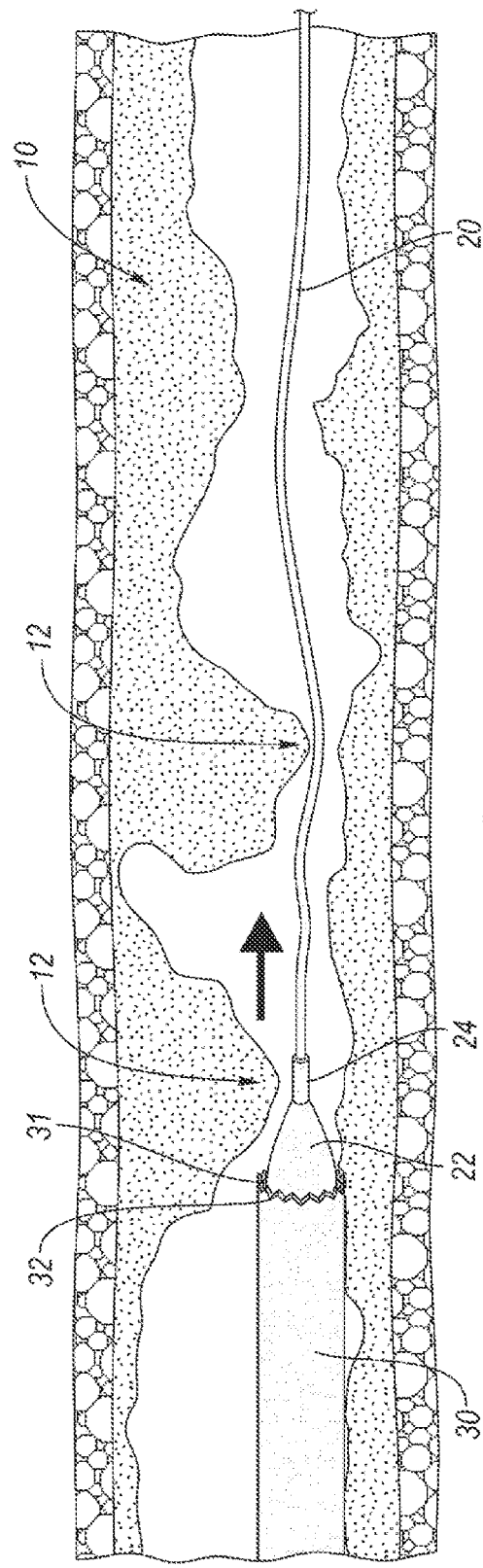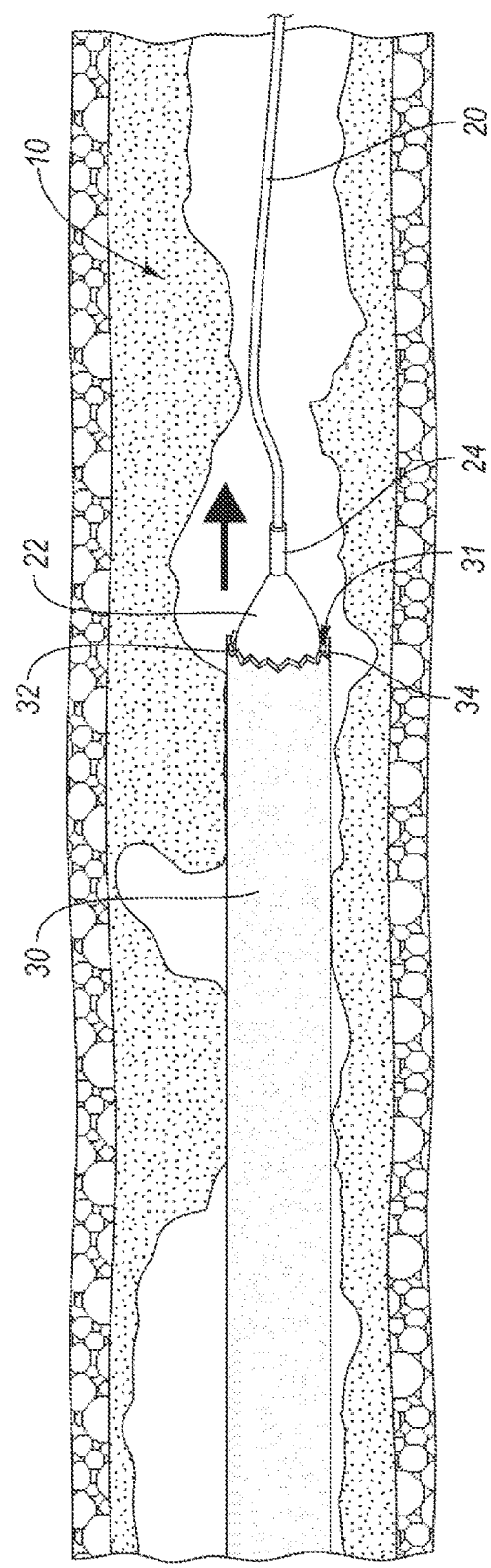

ADJUSTABLE BLOCKAGE-CUTTING DEVICE

TECHNICAL FIELD

The present disclosure relates to a catheter used for percutaneous endovascular procedures, and in particular to a catheter used for treatment of obstructive lesions in a patient's vasculature.

BACKGROUND

The use of percutaneous endovascular procedures has been well established as a minimally invasive technique to deliver a variety of clinical treatments in the patient's vasculature. Such procedures include, for example, the use of a percutaneous endovascular catheter, which may be used in various applications, including delivering and deploying stent grafts.

A common heart disease is atherosclerotic cardiovascular disease, caused by the buildup of plaque or stenoses in blood vessels of a patient. This affliction affects not only veins and arteries, but also dialysis access systems such as fistulas or grafts. Generally, arteries are susceptible to the buildup of plaque. The venous system, however, may have lesions that are generally fibrous in nature, typically in the form of scar tissue. Where there is prolonged or enlarged buildup in the vessels, blood may be dangerously inhibited from passing through the vessel. This can lead to complications of the vasculature system.

SUMMARY

According to one embodiment, an endovascular catheter system is configured to remove a blockage in a vessel of a patient. The catheter comprises an inflatable inner tube and an expandable outer tube. The inner tube is configured to operate in a deflated configuration and an inflated configuration. The outer tube is configured to advance longitudinally over the inner tube when the inner tube is in the deflated configuration. The outer tube includes a leading edge having blocking-cutting features configured to remove at least a portion of the blockage in the vessel. The outer tube is made of a radially-expandable material such that inflation of the inner tube to the inflated configuration when the outer tube is located about the inner tube causes the outer tube to expand radially.

In another embodiment, an endovascular catheter system includes an inner tube extending between a proximal end and a distal end, the distal end being a tapered distal end tapering radially inwardly. A sleeve extends between a proximal end and a distal end and configured to slide over the inner tube. The distal end of the sleeve and the tapered distal end of the inner tube define a radial gap therebetween. The distal end of the sleeve includes blockage-cutting features configured to remove blockages within a blood vessel of a patient.

In another embodiment, a method for treating a blood vessel having blockages therein is provided. The method includes tracking an inner tube along a guidewire to a desired location in the blood vessel, then advancing an outer tube over the inner tube, wherein the outer tube includes blockage-cutting features, then inflating the inner tube to expand the outer tube, then advancing the inner tube and outer tube together through the blood vessel to enable the blockage-cutting feature to cut blockages in the blood vessel.

BRIEF DESCRIPTION OF THE DRAWINGS

FIGS. 1-6 illustrate side interior views of treatment of a blood vessel in sequence, according to one embodiment, in which:

FIG. 1 illustrates an interior of the blood vessel with an inner tube assuming a deflated state located therein;

FIG. 2 illustrates an outer tube or sleeve being slid over the inner tube;

FIG. 3 illustrates the outer tube slid further along the inner tube, and the inner tube being slightly inflated;

FIG. 4 illustrates the inner tube and outer tube advancing together through the vessel as the outer tube cuts blockages from the vessel;

FIG. 5 illustrates the inner tube being further inflated; and

FIG. 6 illustrates the inner tube and outer tube advancing additionally through the vessel as the outer tube cuts blockages from the vessel;

DETAILED DESCRIPTION

Figure 1:
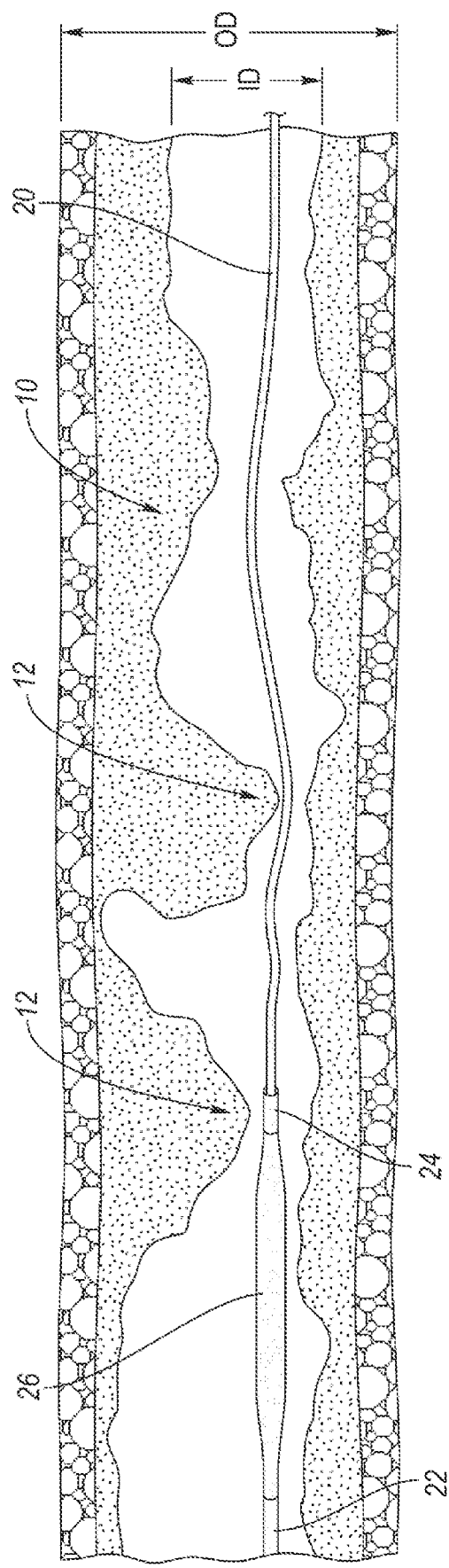

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces faces away from the central axis, or is outboard of another "inner" surface. Terms such as "radial," "diameter," "circumference," etc. also are relative to the central axis. The terms "front," "rear," "upper" and "lower" designate directions in the drawings to which reference is made.

Unless otherwise indicated, for the delivery system the terms "distal" and "proximal" are used in the following description with respect to a position or direction relative to a treating clinician. "Distal" and "distally" are positions distant from or in a direction away from the clinician, and "proximal" and "proximally" are positions near or in a direction toward the clinician. For the stent-graft prosthesis, "proximal" is the portion nearer the heart by way of blood flow path while "distal" is the portion of the stent-graft further from the heart by way of blood flow path.

The following detailed description is merely exemplary in nature and is not intended to limit the invention or the application and uses of the invention. Although the description is in the context of treatment of blood vessels such as the aorta, coronary, carotid and renal arteries, the invention may also be used in any other body passageways where it is deemed useful.

The use of percutaneous endovascular procedures has been well established as a minimally invasive technique to deliver a variety of clinical treatments in the patient's vasculature. One unmet challenge still to be addressed by commercially-available devices is the ability to remove a blockage (such as plaque from hard, calcified occluded lesions) from a blood vessel in order to restore the physiological blood flow through the vessel. References to a "blockage" herein is intended to refer to one or more lesions, stenoses, plaque, or any other similar type of infliction or obstruction within a blood vessel that would constrict blood flow within that vessel.

Therefore, according to various embodiments described herein, an endovascular catheter is disclosed with blockage-cutting features. The blockage-cutting features may include teeth, serrations, or the like and may be located at a leading edge of a lumen in the catheter, for example. As the lumen is advanced along the blood vessel, the blockage-cutting features can cut or score the blockage. Also, the diameter of the lumen may be adjustable. In embodiments explained herein, an inflatable tube may be placed inside the lumen, wherein inflation and deflation of the tube may corresponding expand and contract the lumen.

Referring to FIG. 1, an occluded arterial blood vessel 10 is shown with various blockages 12 that, if left untreated, may inhibit blood flow through the vessel 10. The blood vessel 10 has an outer diameter (OD) and an inner diameter (ID). The OD is defined between an outer wall 14 of the vessel 10. The ID is constricted and varies drastically throughout the vessel 10 due to the prevalence of blockages 12 therein.

A guidewire 20 is shown inserted in the vessel 10. The guidewire 20 can be inserted into the blood vessel 10 via an endovascular procedure in which the guidewire 20 is first inserted into the patient's skin, and is fed along one or more blood vessels until arriving at the desired blood vessel 10 for treatment to take place. The guidewire 20 may be made of various thicknesses, materials, and flexibilities. For example, the guidewire 20 may be a nitinol guidewire such as NITREX or BABYWIRE.

In one embodiment, a shaft or inner tube 22 is provided over the guidewire 20. The inner tube 22 can also be referred to as a lumen, catheter tube, inner shaft, or the like. The inner tube 22 can be or include a dedicated lumen 24 for tracking over the guidewire 20. In application, once the guidewire 20 is properly positioned in the desired vessel 10, the lumen 24 can be slid over the guidewire 20 and advanced along the guidewire 20 until the inner tube 22 itself reaches the desired location in the vessel 10.

FIG. 1 shows the inner tube 22 located at an initial or first linear position within the vessel 10, prior to treatment of the blockages 12. As will be explained below and shown in the remaining Figures, the inner tube 22 can be advanced further into the blood vessel 10 during cutting or scoring of the blockages 12.

The inner tube 22 can also include or be coupled to an inflatable element 26 (e.g., an inflatable balloon or the like) that can adjust in diameter. The inflatable element 26 can assume both a deflated configuration and an inflated configuration. The inflatable element 26 is shown in the deflated configuration in FIG. 1. The inflatable element 26 may be integrally formed with the inner tube 22. For example, the inflatable element 26 and the lumen 24 may be a singular component. The inflatable element 26 may be a sealed chamber disposed radially outward of a central aperture or dedicated lumen of the inner tube 22 (that receives the guidewire 20) so that a fluid medium (e.g., water or saline) performing the inflation of the inflatable element 26 is kept separate and does not contact the guidewire 20. In another embodiment, the inflatable element 26 is a separately-attached component that is configured to assemble to an outer surface of the inner tube 22 or lumen 24. In another embodiment, the inner tube 22 can have a multi-lumen design and structure, with one lumen dedicated to the inflatable element 26 and another dedicated to contain the guidewire 20.

Figure 2:
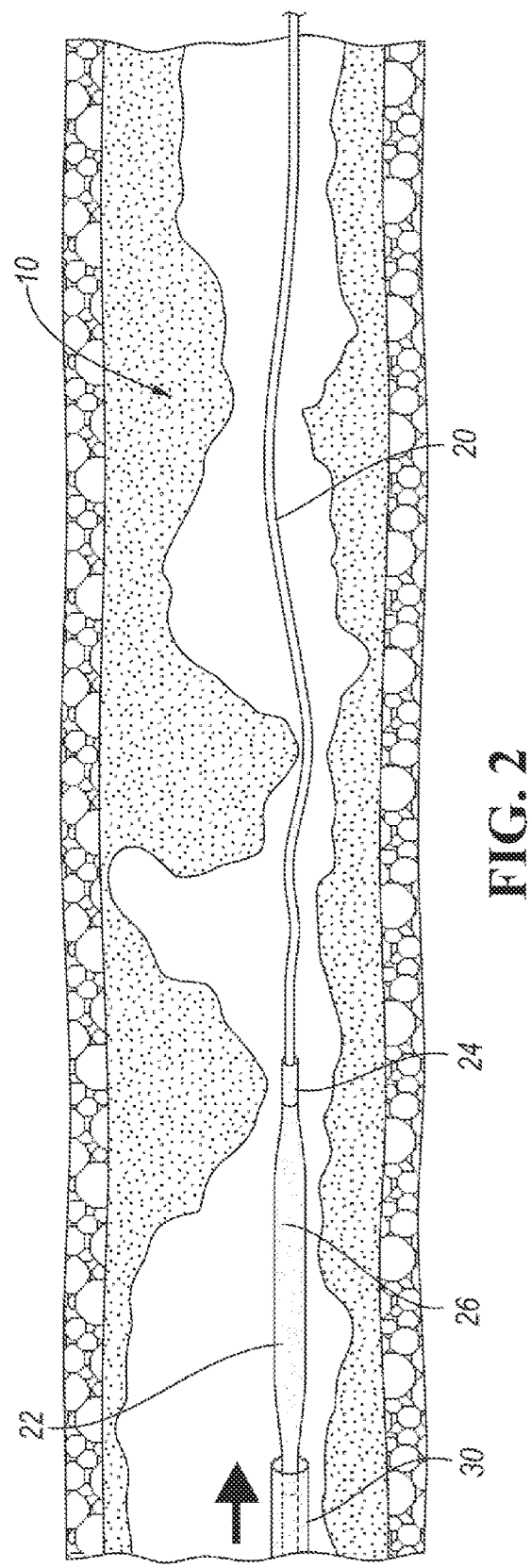

FIG. 2 illustrates an introduction of an outer tube 30 into the treatment area of the vessel 10. The outer tube 30 can also be referred to as a sleeve, lumen, catheter tube, or the like. The outer tube 30 can be a single-lumen configuration with blockage-cutting tips at a distal end thereof (as will be described further below). The outer tube 30 is made of a flexible yet durable material, allowing the outer tube 30 to slide over the outer diameter of the inner tube 22. The outer tube 30 is designed to have rigid longitudinal mechanical properties such that mechanical forces transmitted to the outer tube 30 from the proximal end thereof (e.g., from the operator of the catheter) would be mechanically transferred to a distal end 32 with high efficiency (high "pushability"). The outer tube 30 can be made of, for example, Nitinol, or a combination or Nitinol with other metals and polymers, or other super-elastic alloys due to their elasticity and ability to deform and recoil back to their initial shape without any permanent changes. A material structure similar to that of the covered stents (e.g., polymer fabric sewn onto super-elastic, expandable metal frame) can also be appropriate.

As shown in FIG. 2, the outer tube 30 can be slid over a proximal end of the inner tube 22, and advanced toward the distal end of the inner tube 22. In FIG. 2, the inner tube 22 and its inflatable element 26 are maintained in the deflated configuration, allowing ease of longitudinal movement of the outer tube 30 relative to the inner tube 22. In this configuration, the unbiased, natural-state inner diameter of the outer tube 30 exceeds at least a portion of the outer diameter of the inner tube 22 and/or inflatable element 26 to facilitate the relative movement of the outer tube 30 along the inner tube 22. The inner tube 22, the outer tube 30, and any associated handle or control device (not shown) can be referred to as a catheter or a catheter system for placement along the guidewire 20.

FIG. 3 shows further advancement of the outer tube 30 relative to the inner tube 22. The inner tube 22 and its inflatable element 26 may be maintained in the deflated configuration to allow the further advancement of the outer tube 30 relative to the inner tube 22. During advancement of the outer tube 30, the flexible material properties of the outer tube 30 are such that the outer tube 30 can conform to the shape of the inner tube 22 during such advancement.

Once the distal end 32 outer tube 30 has reached a desired location along the distal portion of the inner tube 22, the inflatable element 26 can be inflated to the inflated configuration. According to one embodiment, the inflation of the inflatable element 26 can be performed by an operator, such as a surgical technician. The operator can pump fluid (e.g., saline, etc.) into the inflatable element 26, thus expanding the diameter of the inflatable element 26. The design of the inflatable element 26 can be such that a direct relationship exists between the inflation pressure used by the operator and the outer dimension of the inflatable element 26, so that inflation to a given pressure will result in a given, known outer diameter of the inflatable element 26. The inflation process would allow the operator to control the dimensional profile of the distal end of the device with respect to the blood vessel through changes in inflation pressure.

The material of the outer tube 30 may be such that it maintains a generally uniform diameter throughout the length of the outer tube 30, regardless of the shape or size of the inner tube 22. This can be seen in FIG. 3, for example, in which the distal end of the inner tube 22 begins to taper inwardly toward the guidewire 20 while the diameter of the outer tube 30 remains constant. This can create a radial gap 31 between the inner tube 22 and the outer tube 30 at the distal end 32 of the outer tube 30. This also keeps radial separation between the blockage-cutting features 34 (described below) and the inner tube 22, allowing the blockage-cutting feature to slice through the blockage without interference from the inner tube 22.

Inflation of the inflatable element 26 can provide at least two functions. First, the inflation couples the inner tube 22 to the outer tube 30 via an outwardly-directed force between an outer surface of the inner tube 22 and an inner surface of the outer tube 30. This force, via inflation, allows the inner tube 22 and outer tube 30 to move along the guidewire 20 in unison; as either the inner tube 22 or outer tube 30 is forced along the guidewire 20, the other of the inner tube 22 or outer tube 30 will be moved along with. It can be said that the inner tube 22 and outer tube 30 are therefore laterally locked. Second, the inflation expands the size of the diameter of the outer tube 30. A controlled amount of inflation may be provided by the operator, and therefore the size of the diameter of the outer tube 30 can be correspondingly controlled. This allows the operator to expand or contract the size of the blockage-cutting tips at the distal end 32 of the outer tube 30, thus altering the size of the cutting to be performed on the blockages 12, as will be described further below.

FIG. 4 shows advancement of the laterally-locked inner tube 22 and outer tube 30 in unison. Since, as explained above, the inner tube 22 and outer tube 30 are locked due to the inflation of the inner tube 22, the inner tube 22 and outer tube 30 can be moved together along the vasculature in the distal direction. This movement may be performed by a surgical technician via a pushing motion, or operation of a handle, for example. In some embodiments, the movement of the outer tube 30 may be only axial in nature (e.g., in the direction of the blood vessel). The axial movement may be continuous or it may be reciprocating (e.g., alternating between pushing and retracting, like a jack-hammer). In other embodiments, the outer tube 30 may be rotated as it is advanced axially. Either type of motion may be performed manually by a physician or technician. However, in other embodiments, the motion may be performed using a motor (e.g., electric motor) coupled to the outer tube 30 and/or inner tube 22. The motor may be controlled by a physician/technician directly or it may be controlled by a robotic surgery system. The direction of rotation and/or axial motion and/or radial velocity of the controlled system can be modulated in relation to the dimension, location, morphology of the vessel and blockage.

As shown in FIGS. 2-4, the distal end 32 of the outer tube 30 is provided with blockage-cutting features 34. The blockage-cutting features may include teeth, serrations, or the like and may be located at a leading edge (e.g., the distal end 32) of the outer tube 30. In one embodiment, the blockage-cutting features are teeth arranged annularly about the circumference of the distal end 32 with the points of the teeth directed parallel to the central longitudinal axis of the outer tube 30. The blockage-cutting features may be triangular in shape, with or without additional serrations thereon. In at least one embodiment, the cutting features extend completely around the circumference of the distal end 32 of the outer tube, although in other embodiments there may be annular gaps between cutting sections.

In another embodiment, the blockage-cutting features may be arranged at a location more proximal than the distal end 32. In an embodiment, the blockage-cutting features may additionally or alternatively face radially outwardly from the central axis of the outer tube 30

As can be seen in comparing FIG. 3 with FIG. 4, as the outer tube 30 is moved along the vessel 10, various blockages 12 have been scraped to widen the overall blood-flow diameter within the vessel 10. As the outer tube 30 is moved along the vessel 10, the blockage-cutting feature 34 engage the blockages 12 and remove at least a portion of the blockages 12. This creates an overall unobstructed blood-flow diameter within the vessel 10 of an amount at least equivalent to the diameter of the outer tube 30.

Figure 5:
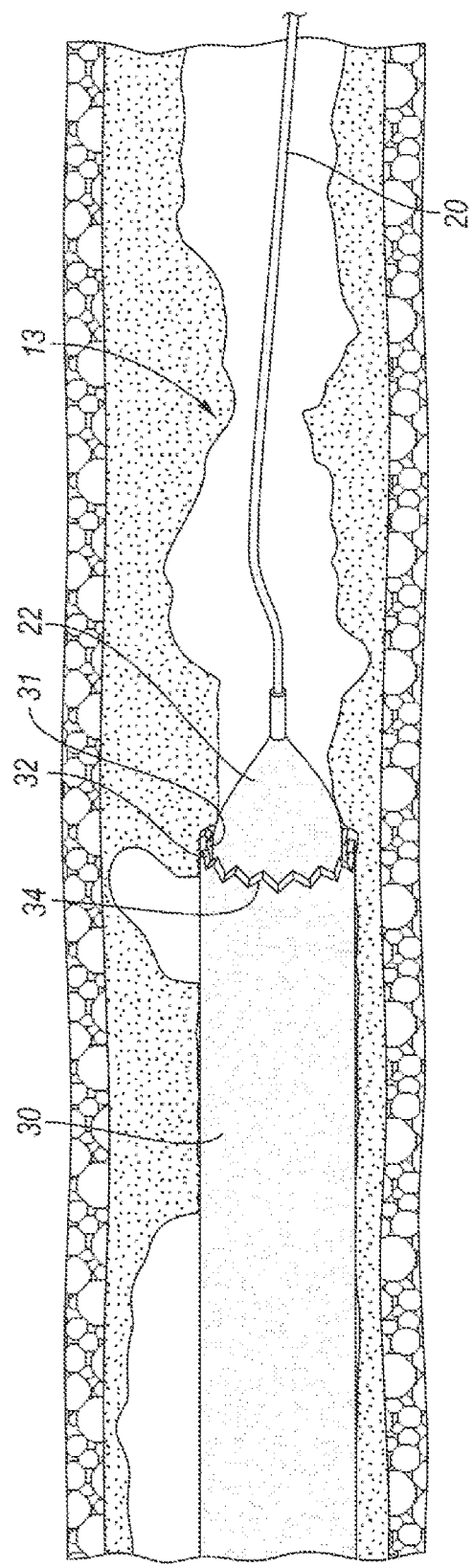

To create a wider diameter of the outer tube 30, and therefore a wider blood-flow diameter within the vessel 10, the inner tube 22 can be further inflated. FIG. 5 illustrates one embodiment of this. In FIG. 5, it can be seen that the inner tube 22 has been further inflated via similar operations as described above. This correspondingly expands the diameter of the outer tube 30, allowing the blockage-cutting features 34 to engage certain blockages 13 that may not have been engageable when the outer tube 30 was its previous diameter (e.g., FIG. 4). By selectively inflating and deflating the inner tube 22 during operation, a surgical technician can select the proper diameter for cutting or scoring the various blockages 12, 13 within the vessel 10. This also allows the overall dimensions of the outer tube 30 to be varied for different sizes of blood vessels. For example, as the inner tube 22 and outer tube 30 are inserted into the patient, they may initially travel along smaller vessels (e.g., iliac artery) until reaching a larger vessel (e.g., aorta). As the inner tube 22 and outer tube 30 enter the aorta, the inner tube 22 can be inflated to a larger size to provide a larger cutting profile than was previously provided during travel in the iliac artery. Also, FIG. 5 shows the overall catheter system being slightly retracted, illustrating one embodiment of proximal and distal movement being possible during a procedure.

In one example, the outer tube 30 and blockage-cutting features 34 may make multiple passes at the same location in a blood vessel to sequentially increase the size of the unobstructed vessel. A first pass may be performed with the outer tube at a first diameter to remove a portion of a blockage. After the first pass, the outer tube 30 and inner tube 22 may be retracted and the diameter of the inflatable element may be increased, thereby also increasing the diameter of the outer tube 30. A second pass may then be performed to remove an additional radial thickness of the blockage due to the increased diameter of the outer tube 30. Additional cycles of retracting, increasing the diameter, and performing another pass may be sequentially performed until the physician has removed a desired amount of the blockage. The number of passes may depend on the magnitude of the blockage, the hardness of the blockage (e.g., harder blockages may need smaller/more passes), the size of the vessel, or other factors. This process may be repeated at multiple axial locations in the vessel.

Figure 6:
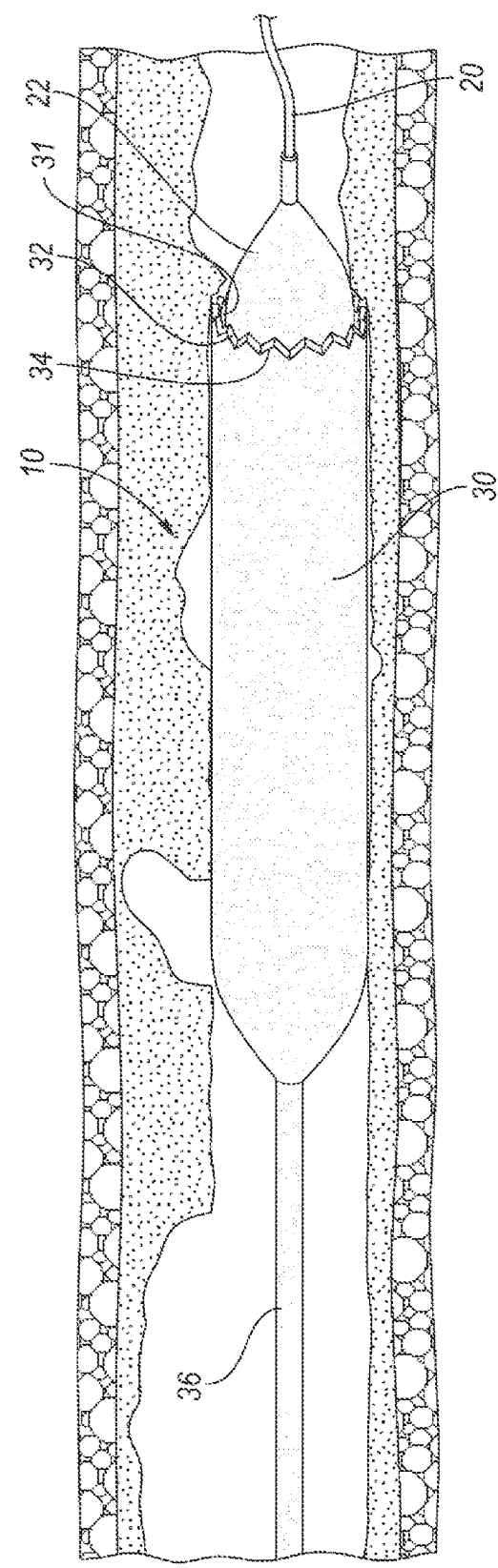

FIG. 6 shows an embodiment similar to FIG. 5, except now showing an outer tube 30 with more flexibility at a proximal end 36 thereof, and the inner tube 22 and outer tube 30 being advanced more through the vessel 10. In this embodiment, the outer tube 30 is relatively rigid at its distal end 32 so that the radial gap 31 is maintained between the inner tube 22 and the outer tube 30. Meanwhile, the outer tube 30 can be relatively flexible (e.g., more flexible than the distal end 32) at its proximal end 36 such that the outer tube 30 conforms to the shape of the inner tube 22 at the proximal end 36. And, with advancement of the catheter system, the blockages 13 once present in FIG. 5 are now removed.

After the blockages are cut or scored according to the teachings above, the blockage can be extracted and removed from the vessel 10. In one example, the removed material may be extracted with a separate removal system, not shown herein. In another example, the cut/scored material may be lodged between the outer tube 30 and the inner tube 22/inflatable element 26. For example, when the inflatable element 26 is deflated, the outer tube 30 may attempt to return to its natural diameter, thereby trapping the removed material between itself and the inflatable element 26. Once a certain amount of the blockage has been removed, the inner and outer tubes may be removed from the body to clear away the removed material. If additional blockages remain to be removed, the inner and outer tubes may be re-inserted and additional removal steps may be performed. This process may be repeated as many times as necessary.

In another example, an aspiration system may be incorporated into the system, either as a separate component or as part of one of the components described herein. The aspiration system may be disposed proximal to the distal end 32 of outer tube 30 such that it can aspirate/suck removed material once it is cut/scored. The aspiration system may be connected to a source of vacuum/suction in the operating room. By intermittently or continuously aspirating, more cutting passes may be performed without removing the outer tube from the body. In embodiments, the teachings above may be implemented into an atherectomy system, such as a rotational or directional atherectomy system, that includes an atherosclerosis-removal feature, for example.

Embodiments disclosed herein illustrate the outer tube 30 being separately attached around the inner tube 22. However, in another embodiment, the outer tube 30 is integral with the inflatable member 26 (e.g., balloon) such that the blockage-cutting features are part of a single, unitary device surrounding the guidewire 20.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. An endovascular catheter system configured to remove a blockage in a vessel of a patient, the endovascular catheter system comprising:
   an inner tube having a deflated state and an inflated state; and
   an outer tube having an unexpanded state and a radially expanded state, the outer tube is configured to advance longitudinally over the inner tube when the inner tube is in the deflated state, the outer tube including a leading edge having blockage-cutting features, the outer tube transitions from the unexpanded state to the radially expanded state when the inner tube transitions from the deflated state to the inflated state to form a lateral lock between the inner tube and the outer tube when advancing the outer tube and the inner tube together through the vessel of the patient so the blockage-cutting features and the inner tube maintain a radial separation allowing the blockage-cutting features to remove or slice through at least a portion of the blockage in the vessel of the patient without interference from the inner tube.

2. The endovascular catheter system of claim 1, wherein the inner tube has a dedicated central lumen configured to travel along an outer surface of a guidewire.

3. The endovascular catheter system of claim 1, wherein the leading edge defines a circumference, and the blockage-cutting features extend from the circumference.

4. The endovascular catheter system of claim 3, wherein the outer tube extends along an axis, and the blockage-cutting features extend in a direction parallel to the axis.

5. The endovascular catheter system of claim 1, wherein the inner tube and outer tube are slideable relative to each other when the inner tube is in the deflated state.

6. The endovascular catheter system of claim 1, wherein the inner tube having a tapered distal end tapering radially inward and extending within the outer tube to beyond the outer tube to define the radial separation between the tapered distal end of the inner tube when advancing the sleeve and the inner tube together through the vessel of the patient.

7. An endovascular catheter system comprising:
   an inner tube extending between a proximal end and a distal end, the distal end being a tapered distal end tapering radially inward; and
   a sleeve extending between a proximal end and a distal end and configured to slide over the inner tube, the sleeve including blockage-cutting features, the tapered distal end of the inner tube extends from within the sleeve to beyond the sleeve to define a radial separation between the distal end of the sleeve and the tapered distal end of the inner tube when advancing the sleeve and the inner tube together through a blood vessel of a patient to form a lateral lock so the radial separation allows the blockage-cutting features to remove or slice through blockages within the blood vessel of the patient without interference from the inner tube.

8. The endovascular catheter system of claim 7, wherein the distal end of the sleeve is rigid to maintain the radial separation.

9. The endovascular catheter system of claim 8, wherein the inner tube has a deflated state and an inflated state, and the sleeve is flexible such that the sleeve expands radially outward as the inner tube inflates to the inflated state.

10. The endovascular catheter system of claim 8, wherein the inner tube has a deflated state and an inflated state, and the sleeve is sized such that the sleeve slides along the inner tube when operating in the deflated state.

11. The endovascular catheter system of claim 10, wherein the sleeve has an unexpanded state and a radially expanded state, the sleeve transitions from the unexpanded state to the radially expanded state when the inner tube transitions from the deflated state to the inflated state to form the lateral lock between the inner tube and the sleeve when advancing the sleeve and the inner tube through the blood vessel of the patient.

12. The endovascular catheter system of claim 7, wherein the sleeve extends along a length, and the blockage-cutting features extend from the distal end of the sleeve in a direction parallel to the length.

13. The endovascular catheter system of claim 7, wherein the blockage-cutting features are teeth or serrations.

14. The endovascular catheter system of claim 8, wherein the inner tube includes a dedicated central lumen configured to track along a guidewire.

15. A method for treating a blood vessel having blockages therein, the method comprising:
 tracking an inner tube along a guidewire to a location in the blood vessel;
 then advancing an outer tube over the inner tube, wherein the outer tube includes blockage-cutting features;
 then inflating the inner tube to expand the outer tube; and
 then advancing the inner tube and outer tube together through the blood vessel to enable the blockage-cutting features to cut blockages in the blood vessel.

16. The method of claim 15, wherein the step of tracking includes tracking a dedicated central lumen of the inner tube along the guidewire.

17. The method of claim 15, further comprising, after the step of advancing the inner tube and outer tube together, further inflating the inner tube to further expand the outer tube.

18. The method of claim 17, further comprising, after the step of further inflating, further advancing the inner tube and outer tube together.

19. The method of claim 15, wherein the step of inflating locks the outer tube to the inner tube.

20. The method of claim 15, further comprising, after the step of advancing the inner tube and outer tube together, deflating the inner tube and retracting the outer tube from the blood vessel.

* * * * *